United States Patent [19]

Kowalczyk et al.

[11] Patent Number: 5,567,818

[45] Date of Patent: Oct. 22, 1996

[54] PROCESSES FOR PREPARING 2-(1-AZABICYCLO[2.2.2]OCT-3-YL)-1H-BENZ[DE] ISOQUINOLIN-1-ONE DERIVATIVES AND INTERMEDIATES USEFUL THEREIN

[75] Inventors: Bruce A. Kowalczyk, Cupertino; Charles A. Dvorak, Palo Alto, both of Calif.

[73] Assignee: Syntex (U.S.A.) Inc., Palo Alto, Calif.

[21] Appl. No.: 272,715

[22] Filed: Jul. 8, 1994

[51] Int. Cl.⁶ ............................................. C07D 455/08
[52] U.S. Cl. ............................................. 546/97
[58] Field of Search ................................... 546/97

[56] References Cited

U.S. PATENT DOCUMENTS 4,077,958  3/1978  Wade et al. ............................... 544/161
5,202,318  4/1993  Berger et al. ............................. 514/211
5,202,333  4/1993  Berger et al. ............................. 514/296

OTHER PUBLICATIONS

CA 115:114377, "2–azabicylo...", Berger et al., EP 430190 Jun. 5, 1991.
CA 119:139153, "2–quinuclidnyl–3–yl...", Clark et al, J. Med. Chem. 36(18) 2645–57, 1993.

*Primary Examiner*—Sharon Gibson
*Assistant Examiner*—Catherine Kilby Scalzo
*Attorney, Agent, or Firm*—Heller Ehrman White & McAuliffe

[57] ABSTRACT

This invention relates to processes for preparing 2-(1-azabicyclo[2.2.2]oct-3-yl)-2,3,3a,4,5,6-tetrahydro-1H-benz[de]isoquinolin-1-one, particularly 2-(1-azabicyclo[2.2.2]oct-3S-yl)-2, 3,3aS,4,5,6-tetrahydro-1H-benz[de]isoquinolin-1-one, and to intermediates useful in such processes.

31 Claims, No Drawings

PROCESSES FOR PREPARING 2-(1-AZABICYCLO[2.2.2]OCT-3-YL)-1H-BENZ[DE] ISOQUINOLIN-1-ONE DERIVATIVES AND INTERMEDIATES USEFUL THEREIN

BACKGROUND OF THE INVENTION

1. Field of the Invention

This invention relates to novel processes for preparing 2-(1-azabicyclo[2.2.2]oct-3-yl)-2,4,5,6-tetrahydro-1H-benz[de]isoquinolin-1-one and 2-(1-azabicyclo[2.2.2]oct-3-yl)-2,3,3a,4,5,6-hexahydro-1 H-benz[de]isoquinolin-1-one and the pharmaceutically acceptable salts thereof, which are 5-HT$_3$ receptor antagonists. This invention also relates to 2-(1-azabicyclo[2.2.2]oct-3-yl)-3-hydroxy-2,3,3a,4,5,6-hexahydro-1H-benz[de]isoquinolin-1-one and salts thereof, which are useful synthetic intermediates, and the processes for their preparation.

2. Description of the Field 2-(1-Azabicyclo[2.2.2]oct-3-yl)-2,3,3a,4,5,6-hexahydro-1H-benz[de]isoquinolin-1-one and 2-(1-azabicyclo[2.2.2]oct-3-yl)-2,4,5,6-tetrahydro-1H-benz[de]isoquinolin-1-one and the pharmaceutically acceptable salts, individual stereoisomers and mixture of stereoisomers thereof are 5-HT$_3$ receptor antagonists. In addition, 2-(1-azabicyclo[2.2.2]oct-3-yl)-2,4,5,6-tetrahydro-1H-benz[de]isoquinolin-1-one and the salts, individual stereoisomers and mixture of stereoisomers thereof are useful in the preparation of 2-(1-azabicyclo[2.2.2]oct-3-yl)-2,3,3a,4,5,6-hexahydro-1H-benz[de]isoquinolin-1-one. Methods for using these 5-HT$_3$ antagonists and certain processes for their preparation, different from those described herein, are described in U.S. Pat. No. 5,202,333.

SUMMARY OF THE INVENTION

This invention relates to a compound named 2-(1-azabicyclo[2.2.2]oct-3-yl)-3-hydroxy-2,3,3a,4,5,6-hexahydro-1 H-benz[de]isoquinolin-1-one and salts, individual stereoisomers and mixtures of stereoisomers thereof.

A second aspect of this invention relates to a process for preparing 2-(1-azabicyclo[2.2.2]oct-3-yl)-3-hydroxy-2,3,3 a,4,5,6-hexahydro-1 H-benz[de]isoquinolin-1-one and salts, individual stereoisomers and mixtures of stereoisomers thereof, which process comprises:

(A) reducing 2-(1-azabicyclo[2.2.2]oct-3-yl)-2,3-dihydro-1H-benz[de]isoquinolin-1,3-dione to give a diastereomeric mixture of 2-(1-azabicyclo[2.2.2]oct-3-yl)-3-hydroxy-2,3,3a,4,5,6-hexahydro-1H-benz[de]isoquinolin-1-one;

(B) optionally separating the diastereomeric mixture of 2-(1-azabicyclo[2.2.2]oct-3-yl)-3-hydroxy-2,3,3a,4,5,6-hexahydro-1H-benz[de]isoquinolin-1-one into individual stereoisomers or mixtures of stereoisomers;

(C) optionally converting 2-(1-azabicyclo[2.2.2]oct-3-yl)-3-hydroxy-2,3,3a,4,5,6-hexahydro-1H-benz[de]isoquinolin-1-one to an acceptable acid or base addition salt; and (D) optionally converting an acid or base addition salt of 2-(1-azabicyclo[2.2.2]oct-3-yl)-3-hydroxy-2,3,3a,4,5,6-hexahydro-1H-benz[de]isoquinolin-1-one to non-salt form.

A third aspect of this invention relates to a process for preparing 2-(1-azabicyclo[2.2.2]oct-3-yl)-3-hydroxy-2,3,3a,4,5,6-hexahydro-1H-benz[de]isoquinolin-1-one and salts, individual stereoisomers and mixtures of stereoisomers thereof, which process comprises:

(A) reacting 2-oxa-1H-2,4,5,6-tetrahydrobenz[de]naphthal-1-one with 1-azabicyclo[2.2.2]oct-3-ylamine to give a diastereomeric mixture of 2-(1-azabicyclo[2.2.2]oct-3-yl)-3-hydroxy-2,3,3a,4,5,6-hexahydro-1H-benz[de]isoquinolin-1-one;

(B) optionally separating the diastereomeric mixture of 2-(1-azabicyclo[2.2.2]oct-3-yl)-3-hydroxy-2,3,3a,4,5,6-hexahydro-1H-benz[de]isoquinolin-1-one into individual stereoisomers or mixtures of stereoisomers;

(C) optionally converting 2-(1-azabicyclo[2.2.2]oct-3-yl)-3-hydroxy-2,3,3a,4,5,6-hexahydro-1H-benz[de]isoquinolin-1-one to an acceptable acid or base addition salt; and (D) optionally converting an acid or base addition salt of 2-(1-azabicyclo[2.2.2]oct-3-yl)-3-hydroxy-2,3,3a,4,5,6-hexahydro-1H-benz[de]isoquinolin-1-one to non-salt form.

A fourth aspect of this invention relates to a process for preparing 2-(1-azabicyclo[2.2.2]oct-3-yl)-2,4,5,6-tetrahydro-1H-benz[de]isoquinolin-1-one and salts and individual stereoisomers thereof, which process comprises:

(A) dehydrating 2-(1-azabicyclo[2.2.2]oct-3-yl)-3-hydroxy-2,3,3a,4,5,6-hexahydro-1H-benz[de]isoquinolin-1-one to give 2-(1-azabicyclo[2.2.2]oct-3-yl)-2,4,5,6-tetrahydro-1H-benz[de]isoquinolin-1-one (B) optionally separating the 2-(1-azabicyclo[2.2.2]oct-3-yl)-2,4,5,6-tetrahydro-1H-benz[de]isoquinolin-1-one into individual stereoisomers;

(C) optionally converting the 2-(1-azabicyclo[2.2.2]oct-3-yl)-2,4,5,6-tetrahydro-1H-benz[de]isoquinolin-1-one to a pharmaceutically acceptable acid addition salt; and (D) optionally converting an acid addition salt of the 2-(1-azabicyclo[2.2.2]oct-3-yl)-2,4,5,6-tetrahydro-1H-benz[de]isoquinolin-1-one into non-salt form.

A fifth aspect of this invention relates to a process for preparing 2-(1-azabicyclo[2.2.2]oct-3-yl)-2,3,3a,4,5,6-hexahydro-1H-benz[de]isoquinolin-1-one and pharmaceutically acceptable salts, individual stereoisomers and mixtures of stereoisomers thereof, which process comprises:

(A) dehydrating 2-(1-azabicyclo[2.2.2]oct-3-yl)-3-hydroxy-2,3,3a,4,5,6-hexahydro-1H-benz[de]isoquinolin-1-one to give 2-(1-azabicyclo[2.2.2]oct-3-yl)-2,4,5,6-tetrahydro-1H-benz[de]isoquinolin-1-one;

(B) hydrogenating the 2-(1-azabicyclo[2.2.2]oct-3-yl)-2,4,5,6-tetrahydro-1H-benz[de]isoquinolin-1-one to give a diastereomeric mixture of 2-(1-azabicyclo[2.2.2]oct-3-yl)-2,3,3a,4,5,6-hexahydro-1H-benz[de]isoquinolin-1-one;

(C) optionally separating the diastereomeric mixture of 2-(1-azabicyclo[2.2.2]oct-3-yl)-2,3,3a,4,5,6-hexahydro-1H-benz[de]isoquinolin-1-one into individual stereoisomers or mixtures of stereoisomers;

(D) optionally converting 2-(1-azabicyclo[2.2.2]oct-3-yl)-2,3,3a,4,5,6-hexahydro-1H-benz[de]isoquinolin-1-one to a pharmaceutically acceptable acid addition salt; and (E) optionally converting an acid addition salt of 2-(1-azabicyclo[2.2.2]oct-3-yl)-2,3,3a,4,5,6-hexahydro-1H-benz[de]isoquinolin-1-one to non-salt form.

A sixth aspect of this invention relates to a process for preparing 2-(1-azabicyclo[2.2.2]oct-3S-yl)-2,3,3aS,4,5,6-hexahydro-1H-benz[de]isoquinolin-1-one and pharmaceutically acceptable salts thereof, which process comprises:

(A) treating 2-(1-azabicyclo[2.2.2]oct-3S-yl)-2,3,3aR,4, 5,6-tetrahydro-1H-benz[de]isoquinolin-1-one with an activated catalyst under an inert atmosphere to give 2-(1-azabicyclo[2.2.2]oct-3S-yl)-2,3,3aS,4,5,6-tetrahydro-1H-benz[de]isoquinolin-1-one; and (B) optionally converting the 2-(1-azabicyclo[2.2.2]oct-3S-yl)-2,3,3aS,4,5,6-tetrahydro-1H-benz[de]isoquinolin-1-one to a pharmaceutically acceptable acid addition salt; and (C) optionally converting an acid addition salt of the 2-(1-azabicyclo[2.2.2]oct-3S-yl)-2,3,3aS,4,5,6-tetrahydro-1H-benz[de]isoquinolin-1-one to non-salt form.

DETAILED DESCRIPTION OF THE INVENTION

Definitions

As used herein:

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts which are pharmaceutically acceptable, as defined above, and which possess the desired pharmacological activity. The compounds of Formula 1, 2, 3, 4 and 6 have a basic nitrogen which is capable of reacting with organic or inorganic acids to form an acid addition salt. Acceptable inorganic acids include hydrochloric acid, hydrobromic acid, sulfuric acid, nitric acid, phosphoric acid, and the like. Acceptable organic acids include acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2,-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In addition, the compound of Formula 3 possesses an acidic proton on the hydroxy group which is capable of reacting with an inorganic or organic base to form a base addition salt. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Optional" or "optionally" means that the subsequently described event or circumstance may or may not occur, and that the description includes instances where the event or circumstance occurs and instances in which it does not. For example, "optionally converting an acid addition salt of the 2-(1-azabicyclo[2.2.2]oct-3S-yl)-2,3,3aS,4,5,6-tetrahydro-1H-benz[de]isoquinolin-1-one to non-salt form" means that the conversion to the non-salt form may or may not be carried out in order for the process described to fall within the invention, and the invention includes those processes wherein the conversion occurs and those processes in which it does not.

Isomerism is the phenomenon wherein compounds have identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are mirror images are termed "enantiomers" or sometimes optical isomers. A carbon atom bonded to four nonidentical substituents is termed a "chiral center".

A compound with one chiral center has two enantiomeric forms of opposite chirality and may exist as either an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer and is termed a "diastereomeric mixture". For the purposes of this application, a mixture of diastereomers containing one or more enantiomeric pairs of diastereomers is termed an "enantiomeric mixture" of diastereomers and a mixture of diastereomers containing two or more diastereomers without their respective enantiomers present is termed a "non-enantiomeric mixture" of diastereomers.

When one chiral center is present a stereoisomer may be characterized by the absolute configuration of that chiral center. Absolute configuration refers to the arrangement in space of the substituents attached to the chiral center. The substituents attached to the chiral center under consideration are ranked in accordance with the Sequence Rule of Cahn, Ingold and Prelog and the absolute descriptor R or S is cited in parentheses followed by a hyphen and the chemical name of compound (e.g., (S)-2-(1-azabicyclo[2.2.2]oct-3-yl)-2,4, 5,6-tetrahydro- 1H-benz[de]isoquinolin-1-one).

For the purposes of this application, when two or more chiral centers are present, the descriptor is cited immediately following the number of the chiral center as it appears in the name of the compound. When a chiral center can be of either configuration individually or as a mixture thereof, in equal amounts or otherwise, or when a chiral center can exist only as a mixture of the two configurations, in equal amounts or otherwise, no descriptor will appear. Accordingly, the compound of Formula 1 in which each of the chiral centers are in an S-configuration, that is, the compound of the following formula:

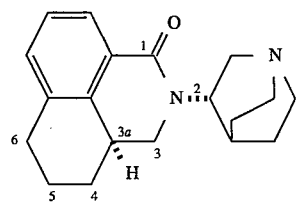

is referred to as 2-(1-azabicyclo[2.2.2]oct-3S-yl)-2,3,3aS,4, 5,6-hexahydro- 1H-benz[de]isoquinolin-1-one.

A compound of Formula 1 in which the 3a-carbon can exist only as a mixture of configurations, that is, the compound of the following formula:

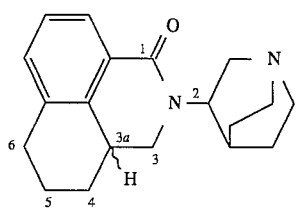

which is the direct product of the hydrogenation of 2-(1-azabicyclo[2.2.2]oct-3-yl)-2,4,5,6-tetrahydro-1H-benz[de]isoquinol in is referred to as 2-(1-azabicyclo[2.2.2]oct-3-yl)-2,3,3a,4,5,6-hexahydro- 1H-benz[de]isoquinolin-1-one.

Preferred Embodiments:

While the broadest definition of this invention is set forth in the Summary of the Invention, certain aspects are preferred. For example, the compound 2-(1-azabicyclo[2.2.2]oct-3S-yl)-3-hydroxy-2,3,3a,4,5,6-hexahydro- 1H-benz[de]isoquinolin-1-one is preferred.

A preferred process for preparing 2-(1-azabicyclo[2.2.2]oct-3-yl)-3-hydroxy-2,3,3a,4,5,6-hexahydro-1H-benz[de]isoquinolin-1-one is that in which the 2-(1-azabicyclo[2.2.2]oct-3-yl)-2,3-dihydro -1H-benz[de]isoquinolin- 1,3-dione is (S)-2-(1-azabicyclo[2.2.2]oct-3-yl)-2,3-dihydro- 1H-benz[de]isoquinolin-1,3-dione and is reduced to give a diastereomeric mixture of 2-(1-azabicyclo[2.2.2]oct-3S-yl)-3-hydroxy-2,3,3a,4,5,6-hexahydro- 1H-benz[de]isoquinolin-1-one; preferably wherein reducing comprises (i) catalytic hydrogenation of the (S)-2-(1-azabicyclo[2.2.2]oct-3-yl)-2,3-dihydro-1H-benz[de]isoquinolin-1,3-dione, preferably an acid addition salt thereof such as trifluoroacetate or camphorsulfonate salt, to give a diastereomeric mixture of 2-(1-azabicyclo[2.2.2]oct-3S-yl)- 2,3,3a,4,5,6-hexahydro-1H-benz[de]isoquinolin-1,3-dione and then (ii) further reduction of the diastereomeric mixture of 2-(1-azabicyclo[2.2.2]oct-3S-yl)- 2,3,3a,4,5,6-hexahydro-1H-benz[de]isoquinolin-1,3-dione with a chemical reducing agent, preferably an alkali metal hydride such as sodium borohydride, to give a diastereomeric mixture of 2-(1-azabicyclo[2.2.2]oct-3S-yl)-3-hydroxy-2,3,3a,4,5,6-hexahydro-1H-benz[de]isoquinolin-1-one.

A preferred process for preparing 2-(1-azabicyclo[2.2.2]oct-3-yl)- 2,4,5,6-tetrahydro-1H-benz[de]isoquinolin-1-one is that in which the 2-(1-azabicyclo[2.2.2]oct-3-yl)-3-hydroxy-2,3,3 a,4,5,6-hexahydro-1H-benz[de]isoquinolin-1-one is 2-(1-azabicyclo[2.2.2]oct-3S-yl)-3-hydroxy- 2,3,3a,4,5,6-hexahydro-1H-benz[de]isoquinolin-1-one and is dehydrated to give (S)-2-(1-azabicyclo[2.2.2]oct-3S-yl)-2,4,5,6-tetrahydro-1H-benz[de]isoquinolin-1-one, preferably wherein the dehydration is catalyzed with hydrochloric acid or sulfuric acid, and the (S)-2-(1-azabicyclo[2.2.2]oct-3S-yl)-3-hydroxy-2,3,3a,4,5,6-hexahydro-1H-benz[de]isoquinolin-1-one is prepared by the preferred process described above.

A preferred process for preparing 2-(1-azabicyclo[2.2.2]oct-3-yl)- 2,3,3a,4,5,6-hexabydro-1H-benz[de]isoquinolin-1-one is that in which the 2-(1-azabicyclo[2.2.2]oct-3-yl)-3-hydroxy -2,3,3 a,4,5,6-hexahydro-1H-benz[de]isoquinolin-1-one is 2-(1-azabicyclo[2.2.2]oct-3S-yl)-3-hydroxy- 2,3,3a,4,5,6-hexahydro-1H-benz[de]isoquinolin-1-one and is dehydrated to give (S)-2-(1-azabi cyclo[2.2.2]oct-3-yl)-2,4,5,6-tetrahydro-1H-benz[de]isoquinolin-1-one, preferably wherein the dehydration is catalyzed with hydrochloric acid or sulfuric acid, the (S)-2-(1-azabicyclo[2.2.2]oct-3-yl)-2,4,5,6-tetrahydro-1H-benz[de]isoquinolin-1-one is hydrogenated in non-salt form to give a diastereomeric mixture of 2-(1-azabicyclo[2.2.2]oct-3S-yl)- 2,3,3a,4,5,6-hexahydro-1H-benz[de]isoquinolin-1-one and the diastereomeric mixture of 2-(1-azabicyclo[2.2.2]oct-3S-yl)-2,3,3a,4,5,6-hexahydro-1H-benz[de]isoquinolin-1-one is separated into individual stereoisomers, preferably by selective crystallization of a pharmaceutically acceptable acid addition salt, preferably hydrochloride salt, of 2-(1-azabicyclo[2.2.2]oct-3S-yl)-2,3,3aS,4,5,6-hexahydro-1H-benz[de]isoquinolin-1-one and the 2-(1-azabicyclo[2.2.2]oct-3S-yl)-3-hydroxy- 2,3,3a,4,5,6-hexahydro-1H-benz[de]isoquinolin-1-one is prepared by the preferred process described above.

A preferred process for converting 2-(1-azabicyclo[2.2.2]oct-3S-yl)- 2,3,3aR,4,5,6-hexahydro-1H-benz[de]isoquinolin-1-one to 2-(1-azabicyclo[2.2.2]oct-3S-yl)-2,3,3aS,4,5,6-hexahydro-1H-benz[de]isoquinolin-1-one is that in which the 2-(1-azabicyclo[2.2.2]oct-S-yl)-2,3,3aR,4,5,6-tetrahydro-1H-benz[de]isoquinolin-1-one is 2-(1-azabicyclo[2.2.2]oct-3S-yl)- 2,3,3aR,4,5,6-hexahydro-1H-benz[de]isoquinolin -1-one hydrochloride.

Processes of the Invention:

The processes of this invention are depicted in the following reaction scheme:

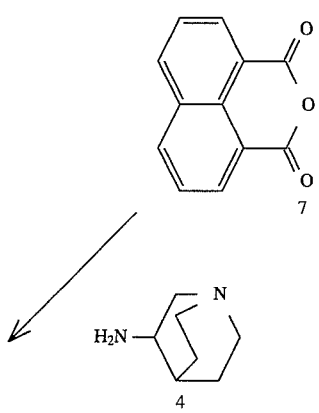

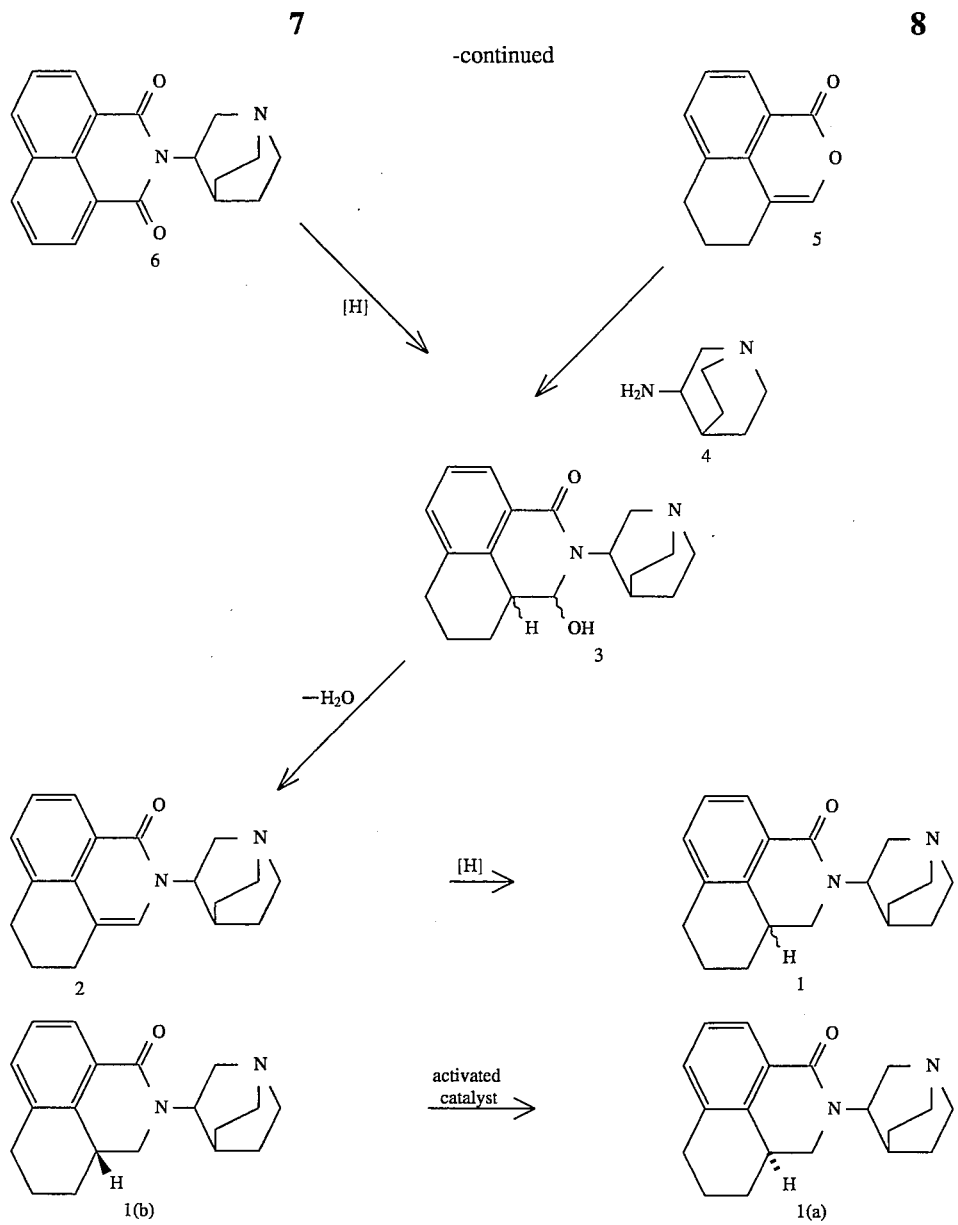

in which Formulae 1 and 3 represent a diastereomeric mixture, enantiomeric or otherwise, Formulae 1 (a) and 1 (b) represent an individual diastereomer or a non-enantiomeric mixture of diastereomers and Formulae 2, 4 and 6 represent an individual enantiomer or an enantiomeric mixture, racemic or otherwise.

A diastereomeric mixture of 2-(1-azabicyclo[2.2.2]oct-3-yl)- 2,3,3a,4,5,6-hexahydro-1H-benz[de]isoquinolin-1-one (Formula 1) is prepared by hydrogenating 2-(1-azabicyclo[2.2.2]oct-3-yl)-2,4,5,6-tetrahydro- 1H-benz[de]isoquinolin-1-one (Formula 2). Preferably the hydrogenation is carried out with the non-salt form of the compound of Formula 2 and in the presence of catalyst (e.g., 10% palladium on carbon (10% Pd/C), platinum(IV) oxide (PtO$_2$), nickel, 5% rhodium on alumina (5% Rh/Al$_2$O$_3$), 20% palladium hydroxide on carbon (Pearlman's catalyst), 5% palladium on barium sulfate (5% Pd/BaSO$_4$), 5% palladium on alumina (5% Pd/Al$_2$O$_3$), 10% palladium on strontium carbonate (10% Pd/SrCO$_3$), etc., preferably 10% Pd/C) and in a suitable organic solvent, typically an ether, alcohol, carboxylic acid, ester, amide or aromatic hydrocarbon and preferably an ether (e.g., tetrahydrofuran (THF), ethanol, acetic acid, ethyl acetate, N,N-dimethylformamide (DMF), toluene, etc., preferably THF), at 10° to 40° C., typically at 15° to 30° C. and preferably at approximately 20° C., and at 0 to 20 psig, typically at 0 to 15 psig and preferably at approximately 5 psig, and requires 20 to 144 hours. The preparation of a compound of Formula 1 is specifically described in Example 7.

Alternatively, the hydrogenation is carried out with an acid addition salt, preferably the hydrochloride salt, of the compound of Formula 2 in the presence of catalyst, typically a palladium catalyst and preferably 10% Pd/C, and in a suitable organic solvent, typically an alcohol or ester or a mixture of alcohol and water and preferably a mixture of alcohol and water (e.g., ethanol, ethyl acetate, 1/10 to 10/1 ethanol/water, etc., preferably approximately 2.4/1 ethanol/water), at 10° to 30° C., typically at 15° to 25° C. and preferably at approximately 20° C., and at 0 to 50 psig, typically at 0 to 20 psig and preferably at approximately 5 psig, and requires 3 to 64 hours.

The compound of Formula 2 is prepared by dehydrating 2-(1-azabicyclo[2.2.2]oct-3-yl)-3-hydroxy-2,3,3a,4,5,6-hexahydro- 1H-benz[de]isoquinolin-1-one (Formula 3). The dehydration is carried out by acid catalysis (e.g., concentrated hydrochloric acid in water, concentrated hydrochloric acid in THF, hydrogen chloride in isopropanol, sulfuric acid in water and ethanol, etc., preferably concentrated hydrochloric acid in water or sulfuric acid in water and ethanol) at −40° to 40° C., typically at −20° to 0° C. and preferably at approximately −10° C., and requires 0.1 to 24 hours. The preparation of a compound of Formula 2 is specifically described in Examples 2 (b), 4 (b) and 6 (b).

A diastereomeric mixture of the compound of Formula 3 is prepared by reducing 2-(1-azabicyclo[2.2.2]oct-3-yl)-2,3-dihydro- 1H-benz[de]isoquinolin-1,3-dione (Formula 6). The reduction can be effected by a two-step process comprising (i) catalytic hydrogenation of the compound of Formula 6, preferably an acid addition salt thereof such as trifluoroacetate or camphorsulfonate salt, to give a diastereomeric mixture of 2-(1-azabicyclo[2.2.2]oct-3-yl)-2,3,3a, 4,5,6-hexahydro- 1H-benz[de]isoquinolin-1,3-dione and then (ii) further reducing the 2-(1-azabicyclo[2.2.2]oct-3-yl)-2,3,3a,4,5,6-hexahydro-1H-benz[de]isoquinolin-1,3-dione with a chemical reducing agent to give a diastereomeric mixture of the compound of Formula 3.

The hydrogenation is carried out in the presence of a suitable catalyst, preferably a palladium catalyst (e.g., 10% Pd/C, 5% palladium on carbon, etc., preferably 10% Pd/C), and in a suitable solvent, typically an alcohol, mixture of alcohols or a mixture of alcohol and water and preferably an alcohol (e.g., ethanol, 1/1 methanol/ethanol, 20/1 to 5/1 ethanol/water, etc., preferably ethanol), at 30° to 70° C., typically at 40° to 60° C. and preferably at approximately 50° C., and at 0 to 150 psig, typically at 0 to 50 psig and preferably at approximately 5 psig, and requires 24 to 144 hours. The reduction of the 2-(1-azabicyclo[2.2.2]oct-3-yl)-2,3,3a,4,5,6-hexahydro- 1H-benz[de]isoquinolin-1,3-dione is carried out with a suitable chemical reducing agent, preferably an alkali borohydride (e.g., sodium borohydride, lithium borohydride, etc., preferably sodium borohydride), in a suitable solvent, typically an alcohol, a mixture of alcohols, a mixture of alcohol and carboxylic acid or a mixture of alcohol and water and preferably an alcohol (e.g., methanol, ethanol, 20/1 to 5/1 ethanol/water, 30/1 to 5/1 methanol/acetic acid, 10/1 to 1/10 ethanol/methanol, etc., preferably ethanol), at −70° to 20° C., preferably −70° to −45° C., and requires 0.5 to 3 hours.

Alternatively, the reduction of the compound of Formula 6 can be effected by a one-step process comprising hydrogenating the non-salt form of the compound of Formula 6 in the presence of a palladium or platinum catalyst (e.g., PtO$_2$, 10% Pd/C, etc., preferably PtO$_2$) and in a suitable solvent, typically an alcohol or a mixture of alcohol and water and preferably an alcohol such as ethanol, at −5° to 65° C., typically at 10° to 30° C. and preferably at approximately 20° C., and at 0 to 200 psig, typically at 100 to 140 psig and preferably at approximately 120 psig, and requires 24 to 170 hours. The preparation of a compound of Formula 3 by the reduction of a compound of Formula 6 is specifically described in Examples 2 (a) and 4 (a).

Alternatively, a diastereomeric mixture of the compound of Formula 3 is prepared by reacting 2-oxa-2,4,5,6-tetrahydrobenz[de]naphthalen-1-one (Formula 5) with 1-azabicyclo[2.2.2]oct-3-ylamine (Formula 4). The reaction can be carried out neat at 130° to 160° C., typically at 140° to 150° C. and preferably at approximately 145° C., and requires 4 to 11 hours. The preparation of a compound of Formula 3 by reacting the compound of Formula 5 with the amine of Formula 4 is specifically described in Example 6 (a).

The compound of Formula 6 can be prepared by reacting 1,8-naphthalic anhydride (Formula 7) with the amine of Formula 4. The reaction is carried out under a nitrogen atmosphere in suitable solvent, typically an alcohol, a mixture of alcohol and xylene, a mixture of alcohol in toluene, or an aromatic hydrocarbon and preferably an alcohol (e.g., isopropanol, n-propanol, n-butanol, 10/1 to 1/10 isopropanol/xylene, 10/1 to 1/10 isopropanol/toluene, toluene, etc., preferably n-propanol), at 75° to 115° C., typically at 90° to 110° C. and preferably at approximately 100° C., and requires 4 to 16 hours. The preparation of the compound of Formula 6 is specifically describe in Examples 1 and 3. The amine of Formula 4 is commercially available or can be readily prepared by methods know to those of ordinary skill in the art.

The compound of Formula 5 can be prepared by hydrogenating 2-oxa-1-oxo-2,4,5,6-tetrahydrobenz[de]naphthalen-3-yl acetate (Formula 9):

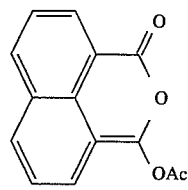

to give 2-oxa-1-oxo-2,3,3a,4,5,6-hexahydrobenz[de]naphthalen-3-yl acetate (Formula 8):

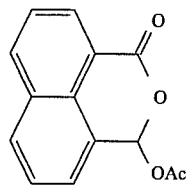

and then treating the compound of Formula 8 with acid. Hydrogenation of the compound of Formula 9 is carried out in the presence of catalyst, typically a palladium catalyst and preferably 10% Pd/C, and in a suitable solvent, typically an ester and preferably ethyl acetate, at 10° to 30° C., typically at 15° to 25° C. and preferably at approximately 20° C., and at 0 to 20 psig, typically at 0 to 10 psig and preferably approximately at 0 psig, and requires 4 to 30 hours. Treatment of the compound of Formula 8 with acid is carried out with a suitable inorganic or organic acid, typically an inorganic acid such as hydrochloric acid and preferably 6N hydrochloric acid, at 50° to 105° C., typically at 80° to 105° C. and preferably at approximately 100° C., and requires 0.5 to 4 hours. The preparation of the compound of Formula 5 is specifically described in Example 5.

The compound of Formula 9 can be prepared by hydrogenating 1,8-naphthalic anhydride (Formula 7) to give a mixture of 1,2,3,4-tetrahydro-1,8-naphthalene anhydride (Formula 10 (a)) and 1,2,3,4-tetrahydro-1,8-naphthalenedicarboxylic acid (Formula 10 (b)):

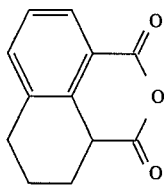

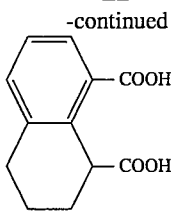

and then reacting the compounds of Formula 10 (a) and 10 (b) with acetic anhydride. Hydrogenation of the compound of Formula 7 is carried out in the presence of a catalyst, typically a palladium catalyst and preferably 10% Pd/C, and in a suitable organic solvent, typically a $(C_{1-5})$alkanoic acid and preferably acetic acid, at 70° to 100° C., typically at 80° to 100° C. and preferably at approximately 90° C., and at 0 to 40 psig, typically at 1 to 10 psig and preferably approximately at 2.5 psig, and requires 24 to 75 hours. The reaction between the compounds of Formulae 10 (a) and 10 (b) and the acetic anhydride is carried out at 20° to 130° C., typically at 20° to 50° C. and preferably at approximately 20° C., and requires 4 to 24 hours.

Depending upon the reaction conditions, isolation/separation techniques and starting materials, the compounds of Formulae 1, 2, 3, 4 and 6 may be converted to or prepared as their non-salt or salt forms. For example, the compound of Formula 6 may be utilized in the processes of this invention as its non-salt or acid addition salt form in order for the process described to fall within the invention, and the invention includes those processes wherein the compound of Formula 6 is in non-salt form and those processes wherein the compound of Formula 6 is an acid addition salt. Similarly, when the compound of Formula 3 is dehydrated with acid, the addition salt of the compound of Formula 2 is formed, which may or may not be subsequently converted to the non-salt form of the compound of Formula 2 before hydrogenating. Accordingly, while some forms of the compounds of Formulae 1, 2, 3, 4 and 6 are preferred, unless indicated otherwise, the description or naming of a particular compound in the specification or in the claims is intended to include both the non-salt form and salt forms, pharmaceutically acceptable or otherwise, thereof.

The compounds of Formulae 1, 2, 3, 4 and 6 each contain one or more chiral centers and can be separated into or prepared as individual stereoisomers and/or mixtures of stereoisomers. The compounds of Formulae 1, 2, 3, 4 and 6 may exist as individual stereoisomers and/or any mixture of stereoisomers in order for the process described to fall within the invention, and the invention includes those processes wherein individual stereoisomers are used and those processes wherein mixtures of stereoisomers are used. Accordingly, while some stereoisomers or mixtures of stereoisomers of the compounds of Formulae 1, 2, 3, 4 and 6 are preferred, unless indicated otherwise, the description or naming of a particular chiral compound in the specification or in the claims is intended to include individual stereoisomers and the mixtures, racemic or otherwise, thereof.

The individual stereoisomers of the compound of Formula 1 can be separated from a non-enantiomeric mixture of diastereomers of the compound of Formula 1 by chromatography, by separation/resolution techniques based upon differences in solubility, by direct or selective crystallization or by any other method known to one of ordinary skill in the art. For example, 2-(1-azabicyclo[2.2.2]oct-3S-yl)-2,3,3aS, 4,5,6-hexahydro- 1H-benz[de]isoquinolin-1-one hydrochloride is readily prepared from a diastereomeric mixture of 2-(1-azabicyclo[2.2.2]oct-3S-yl)- 2,3,3a,4,5,6-hexahydro-1H-benz[de]isoquinolin-1-one hydrochloride by repeated crystallization from a suitable solvent, typically an alcohol and preferably isopropanol.

The individual stereoisomers of the compound of Formula 1 can be prepared from an enantiomeric mixture of diastereomers of the compound of Formula 1 by reacting the enantiomeric mixture of diastereomers with an optically active acid (e.g., tartaric acid, mandelic acid, malic acid, the 2-arylpropionic acids in general, camphorsulfonic acid, etc.) to form diastereomeric crystalline salts, separating the diastereomeric crystalline salts by any of the methods described above for separating diastereomers and then recovering a pure diastereomeric mixture of the compound of Formula 1, along with the optically active acid, by any practical means that would not result in racemization. A more detailed description of the techniques applicable to the preparation of stereoisomers can be found in Jean Jacques, Andre Collet, Samuel H. Wilen, Enantiomers, Racemates and Resolutions, John Wiley & Sons, Inc. (1981).

A non-enantiomeric mixture of diastereomers of the compound of Formula 1 is prepared by proceeding as in Reaction Scheme I and hydrogenating an individual enantiomer of the compound of Formula 2. The individual enantiomers of Formula 2 can be separated from an enantiomeric mixture of the compound of Formula 2 by any of the separation/ resolution techniques described above. Preferably, the individual enantiomers of Formula 2 are prepared by proceeding as in Reaction Scheme I and dehydrating the corresponding non-enantiomeric mixture of diastereomers of the compound of Formula 3 (i.e., a diastereomeric mixture of 2-(1-azabicyclo[2.2.2]oct-3R-yl)-3-hydroxy-2,3,3a,4,5,6-hexahydro- 1H-benz[de]isoquinolin-1-one or a diastereomeric mixture of 2-(1-azabicyclo[2.2.2]oct-3S-yl)-3-hydroxy-2,3,3a,4,5,6-hexahydro- 1H-benz[de]isoquinolin-1-one). The non-enantiomeric mixture of diastereomers of the compound of Formula 3 is prepared by proceeding as in Reaction Scheme I and reducing an individual enantiomer of the compound of Formula 6 or by reacting the compound of Formula 5 with an individual enantiomer of the amine of Formula 4.

An individual enantiomer of the compound of Formula 6 can be separated from an enantiomeric mixture of a compound of Formula 6 by any of the separation/resolution techniques described above or can be prepared by proceeding as in Reaction Scheme I and reacting the compound of Formula 7 with an individual enantiomer of the amine of Formula 4. The individual enantiomers of the amine of Formula 4 can be separated from a enantiomeric mixture of the amine of Formula 4 by any of the applicable separation/ resolution techniques described above. Alternatively, (S)-1-azabicyclo[2.2.2]oct-3-ylamine can be prepared by reacting 1-azabicyclo[2.2.2]oct-3-one with an (R)-α-alkylbenzylamine, preferably (R)-1-phenylethylamine, to give the corresponding (R)-N-(α-alkylbenzyl)-3-(1-azabicyclo[2.2.2] octan)imine, reducing the imine to give the corresponding N-(1R-phenylalkyl)- 1-azabicyclo[2.2.2]oct-3S-ylamine and then hydrogenolyzing. The reaction with the (R)-α-alkylbenzylamine is carried out in the presence of lithium oxide in a suitable organic solvent, typically an ether and preferably THF, at 10° to 40° C., typically at 15° to 30° C. and preferably at approximately 20° C., and requires 12 to 84 hours. The reduction of the imine can be carried out by catalytic hydrogenation or with a suitable chemical reducing agent.

Hydrogenation of the imine is carried out in the presence of a suitable catalyst, preferably 5%Pt/C, and in a suitable organic solvent, typically an alcohol and preferably ethanol, at 10° to 40° C., typically at 15° to 30° C. and preferably at approximately 20° C., and at 0 to 100 psig, typically at 5 to 50 psig and preferably at approximately 20 psig, and requires 1 to 48 hours. Alternatively, the imine can be reduced with a suitable chemical reducing agent, preferably an alkali borohydride (e.g., sodium borohydride, lithium borohydride, etc., preferably sodium borohydride), in a suitable organic solvent, typically an alcohol and preferably ethanol, at −15° to 50° C., typically at 15° to 30° C. and preferably at approximately 20° C., and requires 15 minutes to 3 hours.

The hydrogenolyzation is effected by hydrogenation the N-(1R-phenylalkyl)- 1-azabicyclo[2.2.2]oct-3S-ylamine in the presence of a suitable catalyst (e.g., 10% Pd/C, 20% Pd/C, etc., preferably 10% Pd/C) and in a suitable organic solvent, typically an alcohol and water mixture and preferably 5/1 to 2/1 ethanol/water, at 10° to 40° C., typically at 15° to 30° C. and preferably at approximately 20° C., and at 0 to 100 psig, typically at 0 to 20 psig and preferably at approximately 5 psig, and requires 5 to 48 hours. Proceeding similarly but replacing the (R)-α-alkylbenzylamine with (S)-α-alkylbenzylamine, (R)-1-azabicyclo[2.2.2]oct-3-ylamine can be prepared.

2-(1-Azabicyclo[2.2.2]oct-3-yl)-2,3,3aR,4,5,6-hexahydro-1H-benz[de]isoquinolin-1-one (Formula 1(b)) can be converted to 2-(1-azabicyclo[2.2.2]oct-3-yl)-2,3,3aS,4,5,6-hexahydro-1H-benz[de]isoquinolin-1-one (Formula 1(a)). The conversion can be effected by treating the acid addition salt, preferably the hydrochloride salt, of a compound of Formula 1(b) with activated catalyst (i.e., a catalyst, typically a palladium catalyst and preferably 10% Pd/C, which has been aerated with hydrogen for 1 to 24 hours, typically for 1 to 10 hours and preferably for at least 3 hours) under an inert atmosphere (e.g., nitrogen or argon, preferably nitrogen) and in a suitable solvent, preferably an alcohol or a mixture of alcohol and water and preferably a mixture of alcohol and water (e.g., ethanol, 1/1 to 5/1 ethanol/water, etc., preferably approximately 3/1 ethanol/water) for 20 to 96 hours, typically 40 to 60 hours and preferably for at least 48 hours. The treatment is repeated (i.e., aerating with hydrogen and then with the inert gas) until the conversion is complete (e.g., 1 to 10 times). The conversion of 2-(1-azabicyclo[2.2.2]oct-3S-yl)-2,3,3aR,4,5,6-hexahydro-1H-benz[de]isoquinolin-1-one hydrochloride to 2-(1-azabicyclo[2.2.2]oct-3S-yl)- 2,3,3aS,4,5,6-hexahydro-1H-benz[de]isoquinolin-1-one is further described in Example 8.

Alternatively, the conversion of a compound of Formula 1 (b) to a compound of Formula 1 (a) can be effected by treating the non-salt form of a compound of Formula 1(b) with activated catalyst (i.e., a catalyst, typically a palladium catalyst and preferably 10% Pd/C, which has been aerated with hydrogen for 2 to 96 hours, typically for 2 to 10 hours and preferably for at least 4 hours) under an inert atmosphere (e.g., nitrogen or argon, preferably nitrogen) and in a suitable organic solvent, typically an ether or alcohol and preferably an ether (e.g., THF, ethanol, etc., preferably THF), for 20 to 120 hours, typically for 40 to 60 hours and preferably for at least 48 hours. The treatment is repeated (i.e., aerating with hydrogen and then with the inert gas) until the conversion is complete (e.g., 1 to 20 times).

In summary, an exemplary method of practicing the processes of this Invention is one in which:

(A) (i) an acid addition salt, preferably trifluoroacetate salt or camphorsulfonate salt, of (S)-2-(1-azabicyclo[2.2.2]oct-3-yl)-2,3-dihydro-1H-benz[de]isoquinolin-1,3-dione is hydrogenated in the presence of a catalyst to give a diastereomeric mixture of the corresponding acid addition salt of (S)-2-(1-azabicyclo[2.2.2]oct-3-yl)-2,3,3a,4,5,6-hexahydro- 1H-benz[de]isoquinolin-1,3-dione, (ii) the diastereomeric mixture of the acid addition salt of (S)-2-(1-azabicyclo[2.2.2]oct-3-yl)-2,3,3a,4,5,6-hexahydro-1H-benz[de]isoquinolin-1,3-dione is reduced with an alkali borohydride to give a diastereomeric mixture of the non-salt form of 2-(1-azabicyclo[2.2.2]oct-3S-yl)- 3-hydroxy-2,3,3a,4,5,6-hexahydro-1H-benz[de]isoquinolin-1-one, (B) the diastereomeric mixture of the non-salt form of 2-(1-azabicyclo[2.2.2]oct-3S-yl)-3-hydroxy-2,3,3a,4,5,6-hexahydro-1H-benz[de]isoquinolin-1-one is dehydrated with acid, preferably hydrochloric or sulfuric acid, to give the corresponding acid addition salt of (S)-2-(1-azabicyclo[2.2.2]oct-3-yl)-2,4,5,6-tetrahydro-1H-benz[de]isoquinolin-1-one, (C) the acid addition salt of (S)-2-(1-azabicyclo[2.2.2]oct-3-yl)- 2,4,5,6-tetrahydro-1H-benz[de]isoquinolin-1-one is converted to non-salt form, (D) the non-salt form of (S)-2-(1-azabicyclo[2.2.2]oct-3-yl)- 2,4,5,6-tetrahydro-1H-benz[de]isoquinolin-1-one is hydrogenated in the presence of a palladium catalyst to give a diastereomeric mixture of the non-salt form of 2-(1-azabicyclo[2.2.2]oct-3S-yl)-2,3,3a,4,5,6-hexahydro- 1H-benz[de]isoquinolin-1-one, (E) the diastereomeric mixture of the non-salt form of 2-(1-azabicyclo[2.2.2]oct-3S-yl)-2,3,3a,4,5,6-hexahydro- 1H-benz[de]isoquinolin-1-one is converted to a pharmaceutically acceptable acid addition salt, preferably hydrochloride salt, and (F) the diastereomeric mixture of the pharmaceutically acceptable acid addition salt of 2-(1-azabicyclo[2.2.2]oct-3S-yl)-2,3,3a,4,5,6-hexahydro- 1H-benz[de]isoquinolin-1-one is separated into individual stereoisomers by selective crystallization of the pharmaceutically acceptable acid addition salt of 2-(1-azabicyclo[2.2.2]oct-3S-yl)-2,3,3aS,4,5,6-hexahydro-1H-benz[de]isoquinolin-1-one.

While the process steps described immediately above represent one particular method of practicing the processes of the invention, it should be understood that other variations in the process steps can occur without deviating from the scope of the invention. For example, (S)-2-(1-azabicyclo[2.2.2]oct-3-yl)-2,3-dihydro-1H-benz[de]isoquinolin-1,3-dione may be hydrogenated as the non-salt form to give the non-salt form of 2-(1-azabicyclo[2.2.2]oct-3S-yl)-3-hydroxy-2,3,3a,4,5,6-hexydro- 1H-benz[de]isoquinolin-1-one directly or (S)-2-(1-azabicyclo[2.2.2]oct-3-yl)- 2,4,5,6-tetrahydro-1H-benz[de]isoquinolin-1-one may by hydrogenated as a pharmaceutically acceptable acid addition salt to give a corresponding pharmaceutically acceptable acid addition salt of 2-(1-azabicyclo[2.2.2]oct-3S-yl)-2,3,3a,4,5,6-hexahydro- 1H-benz[de]isoquinolin-1-one.

EXAMPLE 1

(S)-2-(1-Azabicyclo[2.2.2]oct-3-yl)-2,3-dihydro-1H-benz[de]isoquinolin-1,3-dione A mixture of purified 1,8-naphthalic anhydride (10.0 g, 50 mmol) and (S)-1-azabicyclo[2.2.2]oct-3-ylamine (6.7 g, 53 mmol) in 150 mL of isopropanol was heated under reflux under a nitrogen atmosphere for 3 hours. The mixture was distilled to a volume of approximately 100 mL and then cooled for approximately 18 hours giving a crystalline precipitate. The precipitate was recovered by filtration, washed with isopropanol (2×50 mL) and dried in a nitrogen/vacuum oven at 65° C. giving 10.9 g of product. The filtrate was concentrated by rotary evaporation and the residue was dissolved in 20 mL of isopropanol at reflux. The solution was cooled while stirring giving a crystalline precipitate. The precipitate was recovered by filtration, washed with isopropanol (2×10 mL) and dried in a nitrogen/vacuum oven at 65° C. giving 2.4 g of product.

A portion of the product (4.0 g) was eluded through a 2 cm×11 cm flash chromatography column using 0.5% ammonium hydroxide/10% methanol/89.5% methylene chloride. The fraction containing the product was concentrated to a solid which was dissolved in 50 mL of ethyl acetate and 16 mL of isopropanol at reflux. The solution was filtered, stirred for approximately 20 minutes and cooled in an ice-water bath giving a crystalline precipitate. The precipitate was isolated by filtration, washed with 30 mL of ethyl acetate and dried in a nitrogen/vacuum oven giving 2.741 g of product.

The filtrate was concentrated to a solid which was dissolved in 10 mL of ethyl acetate and 3 mL of methanol at reflux. The solution was stirred and cooled in an ice-water bath for 1 hour giving a crystalline precipitate. The precipitate was isolated by filtration and dried in a nitrogen/vacuum oven giving 0.477 g of product. Combining products gave (S)-2-(1-azabicyclo[2.2.2]oct-3-yl)-2,3-dihydro-1H-benz[de]isquinolin-1,3-dione (3.218 g, 10.59 mmol), m.p. 203°–203.4° C. $[\alpha]_D$–69.4° (c=0.74, methanol).

EXAMPLE 2

(S)-2-(1-Azabicyclo[2.2.2]oct-3-yl)-2,4,5,6-tetrahydro-1H-benz[de]isoquinolin-1-one hydrochloride (a) A mixture of (S)-2-(1-azabicyclo[2.2.2]oct-3-yl)-2,3-dihydro-1H-benz[de]isoquinolin-1,3-dione (2.5 g, 8.2 mmol), prepared as in Example 1, and platinum(IV) oxide (0.38 g) in 60 mL of ethanol was stirred at ambient temperature under a hydrogen atmosphere (120 psig) for 118 hours. The reaction mixture was filtered and concentrated giving 2-(1-azabicyclo[2.2.2]oct-3S-yl)- 3-hydroxy-2,3,3a, 4,5,6-tetrahydro-1H-benz[de]isoquinolin-1-one as a foam.

(b) The foam residue was dissolved in 35 mL of isopropanol and then hydrogen chloride in isopropanol (4.4M, 2.2 mL, 9.7 mmol) was added. The mixture was heated under reflux and distilled to a volume of approximately 13 mL. The mixture was then allowed to cool to ambient temperature and stirred for approximately 18 hours. The mixture was cooled for approximately 2 hours in an ice-water bath giving a crystalline product. The product was recovered by filtration and dried in a nitrogen/vacuum oven at 80° C. for 4 hours giving (S)-2-(1-azabicyclo[2.2.2]oct-3-yl)-2,4,5,6-tetrahydro-1H-benz[de]isoquinolin-1-one hydrochloride (1.63 g, 4.9 mmol), m.p. ~300° C. dec. $[\alpha]_D$+54.4° (c=1, chloroform).

EXAMPLE 3

(S)-2-(1-Azabicyclo[2.2.2]oct-3-yl)-2,3-dihydro-1H-benz[de]isoquinolin-1,3-dione trifluoroacetate A mixture of (S)-1-azabicyclo[2.2.2]oct-3-ylamine dihydrochloride (6.0 g, 30.1 mmol) and potassium hydroxide (4 g, 71 mmol) in 30 mL of methanol was stirred at 50° C. for 1 hour. The mixture was diluted with 60 mL of toluene and filtered. The filter cake was washed with 10 mL of toluene and the filtrate was added to a distilling mixture of 1,8-naphthalic anhydride (6.2 g, 31.3 mmol) in 100 mL of n-propanol at a rate so as to maintain a constant volume of distilland. The mixture was distilled to a volume of approximately 75 mL and then heated under reflux for 3 hours. The mixture was cooled to approximately 55° C. and 3 mL of trifluoroacetic acid was added dropwise. The mixture was distilled to a volume of approximately 60 mL, allowed to cool to ambient temperature and stirred for approximately 18 hours giving a crystalline product. The mixture was then cooled in an ice-water bath while stirring for an additional 1.5 hours. The product was isolated by filtration, washed with cold n-propanol and vacuum dried giving (S)-2-(1-azabicyclo[2.2.2]oct-3-yl)- 2,3-dihydro-1H-benz[de]isoquinolin-1,3-dione trifluoroacetate (11.8 g, 28.1 mmol), m.p. 224.7°–225.5° C. $[\alpha]_D$–27.6° (c=1, methanol).

EXAMPLE 4

(S)-2-(1-Azabicyclo[2.2.2]oct-3-yl)-2,4,5,6-tetrahydro-1H-benz[de]isoquinolin-1-one hydrochloride (a) (i) A mixture of (S)-2-(1-azabicyclo[2.2.2]oct-3-yl)-2, 3-dihydro-1H-benz[de]isoquinolin-1,3-dione trifluoroacetate (10.01 g, 23.9 mmol), prepared as in Example 3, and 10% palladium on carbon (7.86 g, water content ≈60%) in 75 mL of ethanol and 75 mL of methanol was stirred at 50° C. under a hydrogen atmosphere (5 psig) for approximately 46 hours. The reaction mixture was filtered and the filter residue was washed with methanol (2×50 mL). The filtrate was concentrated and the residue was dissolved in 100 mL of isopropanol. The solution was concentrated giving 2-(1-azabicyclo[2.2.2]oct-3S-yl)-2,3,3a,4,5,6-hexahydro-1H-benz[de]isoquinolin-1,3-dione trifluoroacetate (9.321 g, 22.14 mmol) as a foam.

(ii) The residue was dissolved in 100 mL of ethanol under a nitrogen atmosphere and the solution was cooled to between –35° and –30° C. Sodium borohydride (1.9 g, 50.2 mmol) in 50 mL of ethanol was added over approximately 40 minutes and the mixture was stirred for 1 hour giving a solution of 2-(1-azabicyclo[2.2.2]oct-3S-yl)-3-hydroxy-2,3, 3a,4,5,6-hexahydro- 1H-benz[de]isoquinolin-1-one.

(b) The solution was diluted with 40 mL of water and 9 mL of concentrated hydrochloric acid was added dropwise. The reaction mixture was allowed to warm to ambient temperature and then stirred for approximately 18 hours. Half of the solution (89 g) was distilled to a volume of approximately 13 mL. The remaining mixture was partitioned between 50 mL of toluene and 5.3 g of 50% sodium hydroxide and 5.0 mL of water. The mixture was warmed to between 50° and 60° C. and the aqueous layer was separated and extracted with toluene (2×50 mL) at 50° to 60° C. The combined toluene layers were dried over magnesium sulfate, filtered and concentrated. The residue was dissolved in 25 mL of isopropanol and then hydrogen chloride in isopropanol (4.4M, 2.5 mL, 11.0 mmol) was added. The solution was stirred for approximately 18 hours and then cooled in an ice-water bath giving a crystalline product. The product was isolated by filtration, washed with 5 mL of isopropanol and dried in a nitrogen/vacuum oven at 65° to 70° C. giving (S)-2-(1-azabicyclo[2.2.2]oct-3-yl)-2,4,5,6-tetrahydro-1H-benz[de]isoquinolin-1-one hydrochloride (2.168 g, 6.6 mmol), m.p. ~300° C. dec. $[\alpha]_D$+54.4° (c=1, chloroform).

EXAMPLE 5

2-Oxa-2,4,5,6-tetrahydrobenz[de]naphthal-1-one

A mixture of 1,8-naphthalic anhydride (10.0 g, 50.5 mmol) and 10% palladium on carbon (2.5 g) in 200 mL of acetic acid was stirred at 90° C. under a hydrogen atmosphere for 73 hours. The reaction mixture was filtered and the filter residue was washed with acetic acid. The filtrate was concentrated and the residue was dissolved in 75 mL of acetic anhydride. The mixture was stirred for approximately 18 hours and concentrated. The residue was dissolved in 20 mL of toluene. The solution was heated and 75 mL of hexane was added at a rate so as to maintain the hexane at reflux. The mixture was cooled in an ice-water bath giving a crystalline product. The product was isolated by filtration, washed with hexane and dried in a nitrogen/vacuum oven at 60° C. giving 2-oxa-1-oxo-2,4,5,6-tetrahydrobenz[de]naphthal-3-ylacetate (5.83 g, 23.9 mmol), m.p. 116°–119° C.

A mixture of 2-oxa-1-oxo-2,4,5,6-tetrahydrobenz[de]naphthal-3-ylacetate (3.04 g, 12.5 mmol) and 10% palladium on carbon (2.0 g) in 50 mL of ethyl acetate was stirred under a hydrogen atmosphere for approximately 18 hours. The reaction mixture was filtered and the filtrate was concentrated and the residue was added to 34 mL of 6N hydrochloric acid. The solution was heated under reflux for 2 hours and then extracted with ethyl acetate (2×50 mL). The combined ethyl acetate extracts were dried over magnesium sulfate, filtered and concentrated. The residue was purified by flash chromatography using 8% ethylacetate/92% toluene with a 32 mm×13 cm column and then 20% methylene chloride/80% toluene with a 32 mm×22 cm column giving 2-oxa-2,4,5,6-tetrahydrobenz[de]naphthal-1-one (0.45 g, 2.42 mmol), m.p. 87°–91° C.

EXAMPLE 6

(S)-2-(1-Azabicyclo[2.2.2]oct-3-yl)-2,4,5,6-tetrahydro-1H-benz[de]isoquinolin-1-one (a) A mixture of 2-oxa-2,4,5,6-tetrahydrobenz[de]naphthal-1-one (0.252 g, 1.36 mmol), prepared as in Example 5, and (S)-1-azabicyclo[2.2.2]oct-3-ylamine (0.1857 g, 1.5 mmol) was heated to between 140° C. and 150° C. for approximately 11 hours. The mixture was dissolved in methanol and concentrated. The residue was purified by flash chromatography using 0.5% ammonium hydroxide/89% methylene chloride/10.5% methanol and then 1% ammonium hydroxide/10% methanol/89% methylene chloride giving a mixture of 2-(1-azabicyclo[2.2.2]oct-3S-yl)-3-hydroxy-2,3,3a,4,5,6-hexahydro-1H-benz[de]isoquinolin-1-one (0.13 g, 0.42 mmol) and (S)-2-(1-azabicyclo[2.2.2]oct-3-yl)-2,4,5,6-tetrahydro- 1H-benz[de]isoquinolin-1-one (0.191 g, 0.655 mmol).

(b) The mixture was dissolved in 0.3 mL of concentrated hydrochloric acid and 1.5 mL of THF and the solution was stirred for 1 minute giving a final solution of (S)-2-(1-azabicyclo[2.2.2]oct-3-yl)-2,4,5,6-tetrahydro- 1H-benz[de]isoquinolin-1-one hydrochloride.

EXAMPLE 7

2-(1-Azabicyclo[2.2.2]oct-3S-yl)-2,3,3aS,4,5,6-hexahydro-1H-benz[de]isoquinolin-1-one hydrochloride A mixture of (S)-2-(1-azabicyclo[2.2.2]oct-3-yl)-2,4,5,6-tetrahydro- 1H-benz[de]isoquinolin-1-one hydrochloride (1875 g, 5.65 mol), prepared as in Example 2, in 6 L of water, 0.46 L of 50% aqueous sodium hydroxide and 10.4 L of toluene was warmed to 50° C. and stirred. The aqueous layer was separated and extracted with toluene (1×6.9 L and then 1×5.8 L). The combined toluene layers were concentrated to approximately 3.61 L and the concentrate was diluted with 45 L of THF.

The organic mixture was stirred with 10% palladium on carbon (2050 g, water content ≈60%) at ambient temperature under a hydrogen atmosphere for 139 hours. The mixture was allowed to stand without stirring under a hydrogen atmosphere for 2 hours and then the atmosphere was purged with nitrogen (8×11 psig). The mixture was filtered, the filter was washed with 6.75 L of THF and the filtrate was distilled to a volume of approximately 7 L. The remaining volume was diluted with 11.0 L of isopropanol and distilled to a volume of approximately 7 L of a solution containing 70% 2-(1-azabicyclo[2.2.2]oct-3S-yl)-2,3,3aS,4,5,6-hexahydro-1H-benz[de]isoquinolin-1-one and 30% 2-(1-azabicyclo[2.2.2]oct-3S-yl)- 2,3,3aR,4,5,6-hexahydro-1H-benz[de]isoquinolin-1-one.

The solution was diluted with 9 L of isopropanol and then 520 mL of concentrated hydrochloric acid was added. The mixture was heated to reflux and then 300 mL of water was added. The mixture was distilled to a volume of approximately 8 L, allowed to cool for 18 hours to ambient temperature and then cooled in an ice-water bath for 4 hours giving a crystalline precipitate. The precipitate was isolated by filtration, washed with 1.3 L of isopropanol and dried at 65° C. for approximately 66 hours giving a dry solid comprising a diastereomeric mixture of 97% 2-(1-azabicyclo[2.2.2]oct-3S-yl)- 2,3,3aS,4,5,6-hexahydro-1H-benz[de]isoquinolin-1-one hydrochloride (A) and 3% 2-(1-azabicyclo[2.2.2]oct-3S-yl)-2,3,3aR,4,5,6-hexahydro- 1H-benz[de]isoquinolin-1-one hydrochloride (B) (1078.7 g, 3.329 mol), m.p. >280° C. and mother liquors comprising a diastereomeric mixture of 13% A and 87% B.

The diastereomeric mixture of 97% A and 3% B was dissolved in 29.3 L of isopropanol. The solution was heated to reflux and 1 L of water and 2.5 L of additional isopropanol was added. The mixture was distilled to a volume of approximately 16 L, cooled over 2 hours to 20° C. and then cooled to 5° C. and stirred for approximately 18 hours giving a crystalline precipitate. The precipitate was isolated by filtration and dried in a nitrogen/vacuum oven at 68° C. giving 99.1% pure 2-(1-azabicyclo[2.2.2]oct-3S-yl)-2,3, 3aS,4,5,6 -hexahydro-1H-benz[de]isoquinolin-1-one hydrochloride (985.1 g, 2.949 mol), m.p. ~303° C. dec.[α]$_D$–90.4° (c=1, chloroform).

EXAMPLE 8

2-(1-Azabicyclo[2.2.2]oct-3S-yl)-2,3,3aS,4,5,6-hexahydro-1H-benz[de]isoquinolin-1-one hydrochloride A mixture of mother liquor (157 g), obtained as in Example 7, and 10% palladium on carbon (107 g, water content ≈60%) in 750 mL of water and 2.25 L of ethanol was alternatively aerated with hydrogen and then nitrogen for 2.5 and 42 hours, 3 and 23 hours, 3 and 70 hours and 2.5 and 26 hours, respectively. The mixture then was aerated with hydrogen for 20 hours and sodium bisulfite (20 g) was added. The mixture was stirred for 10 minutes and then aerated with nitrogen for 3 minutes. The reaction mixture was filtered and the filter residue was washed with 50% ethanol/50% water (2×150 mL).

The filtrate was concentrated to approximately 750 mL and 49 mL of 50% aqueous sodium hydroxide was added. The aqueous mixture was extracted with ethyl acetate (1×1 L and 2×500 mL) and the combined ethyl acetate extracts were dried over sodium sulfate. The ethyl acetate was filtered and concentrated and the residue was dissolved in 1.2 L of ethanol. The solution was cooled in a ice-water bath and hydrogen chloride in ethanol (6.7M, 65.8 mL, 441 mmol) was added. The mixture was allowed to cool for 18 hours to ambient temperature and then cooled for 1 hour in an ice-water bath giving a crystalline precipitate. The precipitate was isolated by filtration, washed with 100 mL of ethanol and dissolved in 1 L of ethanol at reflux.

The ethanol solution was cooled for approximately 18 hours and room temperature and then for 1 hour in an ice-water bath giving a crystalline precipitate. The precipitate was isolated by filtration, washed with 100 mL of ethanol, dried in a nitrogen/vacuum oven at 60° C. for 5 hours and dissolved in 1 L of ethanol at reflux. The solution was allowed to cool to ambient temperature, stirred for 6 hours and then cooled in an ice-water bath for 1 hour giving a crystalline product. The product was isolated by filtration, washed with 100 mL of ethanol, dried in a nitrogen/vacuum oven at 60° C. for approximately 18 hours, sieved with 16 mesh screen and then further dried in a nitrogen/vacuum oven at 60° C. for approximately 18 hours giving 2-(1-azabicyclo[2.2.2]oct-3S-yl)-2,3,3aS,4,5,6-hexahydro-1H-benz[de]isoquinolin-1-one hydrochloride (36.5 g, 109.3 mmol), m.p. ~303° C. $[\alpha]_D$ –90.4° (c=1, chloroform).

We claim:

1. A process for preparing 2-(1-azabicyclo[2.2.2]oct-3-yl)-3-hydroxy- 2,3,3a,4,5,6-hexahydro-1H-benz[de]isoquinolin-1-one and salts, individual stereoisomers and mixtures of stereoisomers thereof, which process comprises:

(A) reducing 2-(1-azabicyclo[2.2.2]oct-3-yl)-2,3-dihydro-1H-benz[de]isoquinolin-1,3-dione to give a diastereomeric mixture of 2-(1-azabicyclo[2.2.2]oct-3-yl)-3-hydroxy-2,3,3a,4,5,6-hexahydro-1H-benz[de]isoquinolin-1-one;

(B) optionally separating the diastereomeric mixture of 2-(1-azabicyclo[2.2.2]oct-3-yl)-3-hydroxy-2,3,3a,4,5,6-hexahydro-1H-benz[de]isoquinolin-1-one into individual stereoisomers or mixtures of stereoisomers;

(C) optionally converting 2-(1-azabicyclo[2.2.2]oct-3-yl)-3-hydroxy- 2,3,3a,4,5,6-hexahydro-1H-benz[de]isoquinolin-1-one to an acceptable acid or base addition salt; and (D) optionally converting an acid or base addition salt of 2-(1-azabicyclo[2.2.2]oct-3-yl)-3-hydroxy-2,3,3a,4,5, 6-hexahydro-1H-benz[de]isoquinolin-1-one to non-salt form.

2. The process of claim 1 in which the 2-(1-azabicyclo[2.2.2]oct-3-yl)-2,3-dihydro-1H-benz[de]isoquinolin-1,3-dione is (S)-2-(1-azabicyclo[2.2.2]oct-3-yl)-2,3-dihydro-1H-benz[de]isoquinolin-1,3-dione and is reduced to give a diastereomeric mixture of 2-(1-azabicyclo[2.2.2]oct-3S-yl)-3-hydroxy-2,3,3a,4,5,6-hexahydro-1H-benz[de]isoquinolin-1-one.

3. The process of claim 2 in which reducing comprises (i) catalytic hydrogenation of the (S)-2-(1-azabicyclo[2.2.2]oct-3-yl)-2,3-dihydro- 1H-benz[de]isoquinolin-1,3-dione to give a diastereomeric mixture of 2-(1-azabicyclo[2.2.2]oct-3S-yl)-2,3,3a,4,5,6-hexahydro- 1H-benz[de]isoquinolin-1,3-dione and then (ii) further reduction of the diastereomeric mixture of 2-(1-azabicyclo[2.2.2]oct-3S-yl)- 2,3,3a,4,5,6-hexahydro-1H-benz[de]isoquinolin-1,3-dione with a chemical reducing agent to give a diastereomeric mixture of 2-(1-azabicyclo[2.2.2]oct-3S-yl)- 3-hydroxy-2,3,3a,4,5,6-hexahydro-1H-benz[de]isoquinolin-1-one.

4. The process of claim 3 in which the (S)-2-(1-azabicyclo[2.2.2]oct-3-yl)-2,3-dihydro-1H-benz[de]isoquinolin-1,3-dione is an acid addition salt thereof and the chemical reducing agent is an alkali metal hydride.

5. The process of claim 4 in which the (S)-2-(1-azabicyclo[2.2.2]oct-3-yl)-2,3-dihydro-1H-benz[de]isoquinolin-3-dione is (S)-2-(1-azabicyclo[2.2.2]oct-3-yl)-2,3-dihydro-1H-benz[de]isoquinolin-1,3-dione trifluoroacetate salt or (S)-2-(1-azabicyclo[2.2.2]oct-3-yl)-2,3-dihydro-1H-benz[de]isoquinolin-3-dione camphorsulfonate and the alkali metal hydride is sodium borohydride.

6. A process for preparing 2-(1-azabicyclo[2.2.2]oct-3-yl)- 2,4,5,6-tetrahydro-1H-benz[de]isoquinolin-1-one and salts and individual stereoisomers thereof, which process comprises:

(A) dehydrating 2-(1-azabicyclo[2.2.2]oct-3-yl)-3-hydroxy- 2,3,3a,4,5,6-hexahydro-1H-benz[de]isoquinolin-1-one to give 2-(1-azabicyclo[2.2.2]oct-3-yl)-2,4,5, 6-tetrahydro-1H-benz[de]isoquinolin-1-one (B) optionally separating the 2-(1-azabicyclo[2.2.2]oct-3-yl)- 2,4,5,6-tetrahydro-1H-benz[de]isoquinolin-1-one into individual stereoisomers;

(C) optionally converting the 2-(1-azabicyclo[2.2.2]oct-3-yl)- 2,4,5,6-tetrahydro-1H-benz[de]isoquinolin-1-one to a pharmaceutically acceptable acid addition salt; and (D) optionally converting an acid addition salt of the 2-(1-azabicyclo[2.2.2]oct-3-yl)-2,4,5,6-tetrahydro-1H-benz[de]isoquinolin-1-one into non-salt form.

7. The process of claim 6 in which the 2-(1-azabicyclo[2.2.2]oct-3-yl)-3-hydroxy-2,3,3a,4,5,6-hexahydro-1H-benz[de]isoquinolin-1-one is 2-(1-azabicyclo[2.2.2]oct-3S-yl)-3-hydroxy-2,3,3a,4,5,6-hexahydro-1H-benz[de] isoquinolin-1-one and is dehydrated to give 2-(1-azabicyclo[2.2.2]oct-3S-yl)-2,4,5,6-tetrahydro-1H-benz[de] isoquinolin-1-one.

8. The process of claim 7 in which the dehydration is catalyzed with hydrochloric acid or sulfuric acid.

9. A process for preparing 2-(1-azabicyclo[2.2.2]oct-3-yl)- 2,4,5,6-tetrahydro-1H-benz[de]isoquinolin-1-one and salts and individual stereoisomers thereof, which process comprises:

(A) reducing 2-(1-azabicyclo[2.2.2]oct-3-yl)-2,3-dihydro-1H-benz[de]isoquinolin-1,3-dione to give a diastereomeric mixture of 2-(1-azabicyclo[2.2.2]oct-3-yl)-3-hydroxy-2,3,3a,4,5,6-hexahydro-1H-benz[de] isoquinolin-1-one;

(B) dehydrating the diastereomeric mixture of 2-(1-azabicyclo[2.2.2]oct-3-yl)- 3-hydroxy-2,3,3a,4,5,6-hexahydro-1H-benz[de]isoquinolin-1-one to give 2-(1-azabicyclo[2.2.2]oct-3S-yl)-2,4,5,6-tetrahydro-1H-benz[de] isoquinolin-1-one;

(C) optionally separating the 2-(1-azabicyclo[2.2.2]oct-3-yl)- 2,4,5,6-tetrahydro-1H-benz[de]isoquinolin-1-one into individual stereoisomers, (D) optionally converting the 2-(1-azabicyclo[2.2.2]oct-3-yl)- 2,4,5,6-tetrahydro-1H-benz[de]isoquinolin-1-one to a pharmaceutically acceptable acid addition salt; and (E) optionally converting an acid addition salt of the 2-(1-azabicyclo[2.2.2]oct-3-yl)-2,4,5,6-tetrahydro-1H-benz[de]isoquinolin-1-one into non-salt form.

10. The process of claim 9 in which the 2-(1-azabicyclo[2.2.2]oct-3-yl)-2,3-dihydro-1H-benz[de]isoquinolin-1,3-dione is (S)-2-(1-azabicyclo[2.2.2]oct-3-yl)-2,3-dihydro-1H-benz[de]isoquinolin-1,3-dione.

11. The process of claim 10 in which reducing comprises (i) catalytic hydrogenation of the (S)-2-(1-azabicyclo[2.2.2]oct-3-yl)-2,3-dihydro-1H-benz[de]isoquinolin-1,3-dione to give a diastereomeric mixture of 2-(1-azabicyclo[2.2.2]oct- 3S-yl)-2,3,3a,4,5,6-hexahydro- 1H-benz[de]isoquinolin-1, 3-dione and then (ii) further reduction of the diastereomeric mixture of 2-(1-azabicyclo[2.2.2]oct-3S-yl)- 2,3,3a,4,5,6-hexahydro-1H-benz[de]isoquinolin-1,3-dione with a chemical reducing agent to give a diastereomeric mixture of 2-(1-azabicyclo[2.2.2]oct-3S-yl)- 3-hydroxy-2,3,3a,4,5,6-hexahydro-1H-benz[de]isoquinolin-1-one.

12. The process of claim 11 in which the (S)-2-(1-azabicyclo[2.2.2]oct-3yl)-2,3-dihydro-1H-benz[de]isoquinolin-3-dione is an acid addition salt thereof and the chemical reducing agent is an alkali metal hydride.

13. The process of claim 12 in which the (S)-2-(1-azabicyclo[2.2.2]oct-3-yl)-2,3-dihydro-1H-benz[de]isoquinolin-3-dione is (S)-2-(1-azabicyclo[2.2.2]oct-3-yl)-2,3-dihydro- 1H-benz[de]isoquinolin-1,3-dione trifluoroacetate or (S)-2-(1-azabicyclo[2.2.2]oct-3-yl)-2,3-dihydro-1H-benz [de]isoquinolin-1,3-dione camphorsulfonate and the alkali metal hydride is sodium borohydride.

14. The process of claim 13 in which the dehydration is catalyzed with hydrochloric acid or sulfuric acid.

15. A process for preparing 2-(1-azabicyclo[2.2.2]oct-3-yl)- 2,3,3a,4,5,6-hexahydro-1H-benz[de]isoquinolin-1-one and pharmaceutically acceptable salts, individual stereoisomers and mixtures of stereoisomers thereof, which process comprises:

(A) dehydrating 2-(1-azabicyclo[2.2.2]oct-3-yl)-3-hydroxy- 2,3,3a,4,5,6-hexahydro-1H-benz[de]isoquinolin-1-one to give 2-(1-azabicyclo[2.2.2]oct-3-yl)-2,4,5, 6-tetrahydro-1H-benz[de]isoquinolin-1-one (B) hydrogenating the 2-(1-azabicyclo[2.2.2]oct-3-yl)-2, 4,5,6-tetrahydro- 1H-benz[de]isoquinolin-1-one to give a diastereomeric mixture of 2-(1-azabicyclo[2.2.2] oct-3-yl)-2,3,3a,4,5,6-hexahydro- 1H-benz[de]isoquinolin-1-one;

(C) optionally separating the diastereomeric mixture of 2-(1-azabicyclo[2.2.2]oct-3-yl)-2,3,3a,4,5,6-hexahydro- 1H-benz[de]isoquinolin-1-one into individual stereoisomers or mixtures of stereoisomers;

(D) optionally converting 2-(1-azabicyclo[2.2.2]oct-3-yl)- 2,3,3a,4,5,6-hexahydro-1H-benz[de]isoquinolin-1-one to a pharmaceutically acceptable acid addition salt; and (E) optionally converting an acid addition salt of 2-(1-azabicyclo[2.2.2]oct-3-yl)-2,3,3a,4,5,6-hexahydro-1H-benz[de]isoquinolin-1-one to non-salt form.

16. The process of claim 15 in which the 2-(1-azabicyclo [2.2.2]oct-3-yl)-3-hydroxy-2,3,3a,4,5,6-hexahydro-1H-benz[de]isoquinolin-1-one is 2-(1-azabicyclo[2.2.2]oct-3S-yl)-3-hydroxy- 2,3,3a,4,5,6-hexahydro-1H-benz[de]isoquinolin-1-one and is dehydrated to give (S)-2-(1-azabicyclo[2.2.2]oct-3-yl)-2,4,5,6-tetrahydro-1H-benz[de] isoquinolin-1-one.

17. The process of claim 16 in which the dehydration is catalyzed with hydrochloric acid or sulfuric acid.

18. The process of claim 17 in which the (S)-2-(1-azabicyclo[2.2.2]oct-3-yl)-2,4,5,6-tetrahydro- 1H-benz[de] isoquinolin-1-one is hydrogenated in non-salt form to give a diastereomeric mixture of 2-(1-azabicyclo[2.2.2]oct-3S-yl)-2,3,3a,4,5,6-hexahydro-1H-benz[de]isoquinolin-1-one.

19. The process of claim 18 in which the diastereomeric mixture of 2-(1-azabicyclo[2.2.2]oct-3S-yl)-2,3,3a,4,5,6-hexahydro-1H-benz[de]isoquinolin-1-one is separated into individual stereoisomers.

20. The process of claim 19 in which the diastereomeric mixture of 2-(1-azabicyclo[2.2.2]oct-3S-yl)-2,3,3a,4,5,6-hexahydro-1H-benz[de]isoquinolin-1-one is a pharmaceutically acceptable acid addition salt thereof and is separated into individual stereoisomers by selective crystallization of a corresponding pharmaceutically acceptable acid addition salt of 2-(1-azabicyclo[2.2.2]oct-3S-yl)-2,3,3aS,4,5,6-hexahydro-1H-benz[de]isoquinolin-1-one.

21. The process of claim 20 in which 2-(1-azabicyclo [2.2.2]oct-3S-yl)- 2,3,3a,4,5,6-hexahydro-1H-benz[de]isoquinolin-1-one hydrochloride is separated into individual stereoisomers by selective crystallization of 2-(1-azabicyclo [2.2.2]oct-3S-yl)-2,3,3aS,4,5,6-hexahydro- 1H-benz[de]isoquinolin-1-one hydrochloride.

22. A process for preparing 2-(1-azabicyclo[2.2.2]oct-3-yl)- 2,3,3a,4,5,6-hexahydro-1H-benz[de]isoquinolin-1-one and pharmaceutically acceptable salts, individual stereoisomers and mixtures of stereoisomers thereof, which process comprises:

(A) reducing 2-(1-azabicyclo[2.2.2]oct-3-yl)-2,3-dihydro- 1H-benz[de]isoquinolin-1,3-dione to give a diastereomeric mixture of 2-(1-azabicyclo[2.2.2]oct-3-yl)- 3-hydroxy -2,3,3a,4,5,6-hexahydro- 1H-benz[de] isoquinolin-1-one;

(B) dehydrating the diastereomeric mixture of 2-(1-azabicyclo[2.2.2]oct-3-yl)-hydroxy- 2,3,3a,4,5,6-hexahydro-1H-benz[de]isoquinolin-1-one to give 2-(1-azabicyclo[2.2.2]oct-3-yl)-2,4,5,6-tetrahydro-1H-benz[de] isoquinolin-1-one; and (C) hydrogenating the 2-(1-azabicyclo[2.2.2]oct-3-yl)-2, 4,5,6-tetrahydro-1H-benz[de]isoquinolin-1-one to give a diastereomeric mixture of 2-(1-azabicyclo[2.2.2]oct-3-yl)-2,3,3a,4,5,6-hexahydro-1H-benz[de]isoquinolin-1-one;

(D) optionally separating the diastereomeric mixture of 2-(1-azabicyclo[2.2.2]oct-3-yl)-2,3,3a,4,5,6-hexahydro-1H-benz[de]isoquinolin-1-one into individual stereoisomers or a mixture of stereoisomers;

(E) optionally converting the 2-(1-azabicyclo[2.2.2]oct-3-yl)- 2,3,3a,4,5,6-hexahydro-1H-benz[de]isoquinolin-1-one to a pharmaceutically acceptable acid addition salt; and (F) optionally converting an acid addition salt of the 2-(1-azabicyclo[2.2.2]oct-3-yl)-2,3,3a,4,5,6-hexahydro-1H-benz[de]isoquinolin-1-one to non-salt form.

23. The process of claim 22 in which the 2-(1-azabicyclo [2.2.2]oct-3-yl)-2,3-dihydro-1H-benz[de]isoquinolin-1,3-dione is (S)-2-(1-azabicyclo[2.2.2]oct-3-yl)-2,3-dihydro-1H-benz[de]isoquinolin-1,3-dione.

24. The process of claim 23 in which reducing comprises (i) catalytic hydrogenation of the (S)-2-(1-azabicyclo[2.2.2] oct-3-yl)-2,3-dihydro-1H-benz[de]isoquinolin-1,3-dione to give a diastereomeric mixture of 2-(1-azabicyclo[2.2.2]oct-3S-yl)-2,3,3a,4,5,6-hexahydro-1H-benz[de]isoquinolin-1,3-dione and then (ii) further reduction of the diastereomeric mixture of 2-(1-azabicyclo[2.2.2]oct-3S-yl)- 2,3,3a,4,5,6-hexahydro-1H-benz[de]isoquinolin-1,3-dione with a chemical reducing agent to give a diastereomeric mixture of 2-(1-azabicyclo[2.2.2]oct-3S-yl)-3-hydroxy-2,3,3a,4,5,6-hexahydro-1H-benz[de]isoquinolin-1-one.

25. The process of claim 24 in which the (S)-2-(1-azabicyclo[2.2.2]oct-3-yl)-2,3-dihydro-1H-benz[de]isoquinolin-1,3-dione is an acid addition salt thereof and the chemical reducing agent is an alkali metal hydride.

26. The process of claim 25 in which the (S)-2-(1-azabicyclo[2.2.2]oct-3-yl)-2,3-dihydro-1H-benz[de]isoquinolin-1,3-dione is (S)-2-(1-azabicyclo[2.2.2]oct-3-yl)-2, 3-dihydro- 1H-benz[de]isoquinolin-1,3-dione trifluoroacetate or (S)-2-(1-azabicyclo[2.2.2]oct-3-yl)-2,3- dihydro-1H-benz[de]isoquinolin-1,3-dione camphorsulfonate and the alkali metal hydride is sodium borohydride.

27. The process of claim 26 in which the dehydration is catalyzed with hydrochloric acid or sulfuric acid to give (S)-2-(1-azabicyclo[2.2.2]oct-3-yl)-2,4,5,6-tetrahydro-1H-benz[de]isoquinolin-1-one.

28. The process of claim 27 in which the (S)-2-(1-azabicyclo[2.2.2]oct-3-yl)-2,4,5,6-tetrahydro-1H-benz[de]isoquinolin-1-one is hydrogenated in its non-salt form to give a diastereomeric mixture of 2-(1-azabicyclo[2.2.2]oct-3S-yl)-2,3,3a,4,5,6-hexahydro-1H-benz[de]isoquinolin-1-one.

29. The process of claim 28 in which the diastereomeric mixture of 2-(1-azabicyclo[2.2.2]oct-3S-yl)-2,3,3a,4,5,6-hexahydro-1H-benz[de]isoquinolin-1-one is separated into individual stereoisomers.

30. The process of claim 29 in which the 2-(1-azabicyclo[2.2.2]oct-3S-yl)-2,3,3a,4,5,6-hexahydro-1H-benz[de]isoquinolin-1-one is a pharmaceutically acceptable acid addition salt thereof and is separated into individual stereoisomers by selective crystallization of a corresponding pharmaceutically acceptable acid addition salt of 2-(1-azabicyclo[2.2.2]oct-3S-yl)-2,3,3aS,4,5,6-hexahydro- 1H-benz[de]isoquinolin-1-one.

31. The process of claim 30 in which 2-(1-azabicyclo[2.2.2]oct-3S-yl)- 2,3,3a,4,5,6-hexahydro-1H-benz[de]isoquinolin-1-one hydrochloride is separated into individual stereoisomers by selective crystallization of 2-(1-azabicyclo[2.2.2]oct-3S-yl)-2,3,3aS,4,5,6-hexahydro- 1H-benz[de]isoquinolin-1-one hydrochloride.

* * * * *

UNITED STATES PATENT AND TRADEMARK OFFICE
CERTIFICATE OF CORRECTION

PATENT NO. : 5,567,818
DATED : Oct. 22, 1996
INVENTOR(S) : Kowalczyk et al.

It is certified that error appears in the above-indentified patent and that said Letters Patent is hereby corrected as shown below:

Claim 5, at column 20, line 2 "[2.2.2]oct-3-yl)-2,3-dihydro-1H-benz[de]isoquinolin-3-di-" should read -- [2.2.2]oct-3-yl)-2,3-dihydro-1H-benz[de]isoquinolin-1,3-di --.

Claim 5, at column 20, line 6 "[de]isoquinolin-3-dione camphorsulfonate and the alkali" should read -- [de]isoquinolin-1,3-dione camphorsulfonate and the alkali --.

Claim 9.(B), at column 20, line 47 "cyclo[2.2.2]oct-3S-yl)-2,4,5,6-tetrahydro-1H-benz[de]" should read -- cyclo[2.2.2]oct-3-yl)-2,4,5,6-tetrahydro-1H-benz[de] --.

Claim 12, at column 21, line 10 "quinolin-3-dione is an acid addition salt thereof and the" should read -- quinolin-1,3-dione is an acid addition salt thereof and the --.

Claim 13, at column 21, line 14 "quinolin-3-dione is (S)-2-(1-azabicyclo[2.2.2]oct-3-yl)-2,3-" should read -- quinolin-1,3-dione is (S)-2-(1-azabicyclo[2.2.2]oct-3-yl)-2,3- --.

Signed and Sealed this

Fourth Day of February, 1997

Attest:

BRUCE LEHMAN

*Attesting Officer*      *Commissioner of Patents and Trademarks*